(12) United States Patent
Holmes et al.

(10) Patent No.: US 9,709,443 B2
(45) Date of Patent: Jul. 18, 2017

(54) DETECTING INCLUSIONS AND DISBONDS IN GREEN MATERIAL REPAIRS WITH THERMOGRAPHY

(71) Applicant: THE BOEING COMPANY, Chicago, IL (US)

(72) Inventors: Tyler M. Holmes, Seattle, WA (US); Gary E. Georgeson, Tacoma, WA (US); Jeffrey G. Thompson, Auburn, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 14/961,494

(22) Filed: Dec. 7, 2015

(65) Prior Publication Data

US 2017/0160139 A1 Jun. 8, 2017

(51) Int. Cl.
G02F 1/01 (2006.01)
G01J 5/10 (2006.01)
G01J 5/00 (2006.01)

(52) U.S. Cl.
CPC ......... *G01J 5/10* (2013.01); *G01J 2005/0077* (2013.01); *G01J 2005/0081* (2013.01)

(58) Field of Classification Search
CPC ............................. G01N 25/72; G01N 33/442
See application file for complete search history.

(56) References Cited

U.S. PATENT DOCUMENTS

| | | | |
|---|---|---|---|
| 9,004,753 B1 | 4/2015 | Maresca, Jr. et al. | |
| 2002/0018510 A1* | 2/2002 | Murphy | G01N 25/72 374/45 |
| 2005/0244975 A1* | 11/2005 | Rakow | G01N 33/442 436/85 |
| 2008/0107147 A1* | 5/2008 | Kollgaard | G01N 25/72 374/5 |
| 2011/0123093 A1* | 5/2011 | Alloo | G01N 25/72 382/149 |
| 2011/0235672 A1 | 9/2011 | Shepard et al. | |
| 2015/0198547 A1* | 7/2015 | Isakov | G01N 25/72 374/121 |

FOREIGN PATENT DOCUMENTS

| | | |
|---|---|---|
| EP | 1334819 A1 | 8/2003 |
| EP | 1391721 A2 | 2/2004 |
| WO | 2006093703 A1 | 9/2006 |

OTHER PUBLICATIONS

Extended European Search Report dated Apr. 20, 2017, for Application No. 16200490.7-1559.

* cited by examiner

*Primary Examiner* — Kiho Kim
(74) *Attorney, Agent, or Firm* — Patterson + Sheridan, LLP

(57) ABSTRACT

Method and apparatus for detecting defects in a laminate of uncured, compacted composite sheets. After a number of plies of composite sheets are arranged and compacted, a burst of heat energy is applied to a top surface of the laminate and a digital thermographic camera captures images of the top surface. A computer processor measures heat characteristics of the top surface to identify regions of the top surface with different heat characteristics. Such different areas are identified as regions that include a defect. The defect regions can be repaired by applying additional compaction and/or by removing at least a portion of some layers, removing any foreign object debris, replacing the layers, and compacting the replaced layers. After any defects are addressed, the laminate is cured.

12 Claims, 6 Drawing Sheets

DETECTING INCLUSIONS AND DISBONDS IN GREEN MATERIAL REPAIRS WITH THERMOGRAPHY

BACKGROUND

Aspects described herein relate to flaw detection in composite laminates, and more specifically, to detecting flaws in green composite materials, which are composite materials that have not yet been cured.

SUMMARY

According to one aspect, a method includes applying a burst of thermal energy to a surface of a plurality of uncured compacted composite layers. The method also includes capturing at least one digital thermographic image of the surface of the uncured compacted composite layers after applying the burst of thermal energy. The method also includes, using a computer processor, analyzing at least one heat characteristic of regions of the uncured compacted composite layers in the at least one digital thermographic image to identify defect regions in which the at least one heat characteristic is different than surrounding regions. The method also includes outputting an alert upon identifying a defect region.

According to one aspect, a system includes a work surface for arranging and compacting uncured composite layers. The system also includes a heat source arranged relative to the surface and operable to provide a burst of thermal energy to a surface of uncured compacted composite layers on the work surface. The system also includes a thermographic digital camera arranged relative to the surface and operable to capture at least one digital thermographic image of the surface of uncured compacted composite layers on the work surface. The system also includes a computer processor in communication with the thermographic digital camera and the heat source. The system also includes a computer memory containing a program that, when executed on the computer processor, performs an operation for processing data, comprising outputting a signal to the heat source to apply a burst of thermal energy to a surface of uncured compacted composite layers. The operation also comprises capturing at least one digital thermographic image of the surface of the uncured compacted composite layers after applying the burst of thermal energy. The operation also comprises analyzing at least one heat characteristic of regions of the uncured compacted composite layers in the at least one digital thermographic image to identify defect regions in which the at least one heat characteristic is different than surrounding regions. The operation also comprises outputting an alert upon identifying a defect region.

According to one aspect, a method includes arranging and compacting a plurality of uncured composite layers. The method also includes applying a burst of thermal energy to a surface of the plurality of uncured compacted composite layers. The method also includes capturing at least one digital thermographic image of the surface of the uncured compacted composite layers after applying the burst of thermal energy. The method also includes using a computer processor, analyzing at least one heat characteristic of regions of the uncured compacted composite layers in the at least one digital thermographic image to identify defect regions in which the at least one heat characteristic is different than surrounding regions. The method also includes, upon identifying a defect region, outputting an alert performing a repair operation on the defect region.

DETAILED DESCRIPTION

In the following, reference is made to aspects presented in this disclosure. However, the scope of the present disclosure is not limited to specific described aspects. Instead, any combination of the following features and elements, whether related to different aspects or not, is contemplated to implement and practice contemplated aspects. Furthermore, although aspects disclosed herein may achieve advantages over other possible solutions or over the prior art, whether or not a particular advantage is achieved by a given aspect is not limiting of the scope of the present disclosure. Thus, the following aspects, features, and advantages are merely illustrative and are not considered elements or limitations of the appended claims except where explicitly recited in a claim(s). Likewise, reference to "the invention" or "the disclosure" shall not be construed as a generalization of any inventive subject matter disclosed herein and shall not be considered to be an element or limitation of the appended claims except where explicitly recited in a claim(s).

Structures, such as wing spars and fuselage barrel sections of aircraft can be made with composite materials. The composite materials are typically formed as a laminate of several plies of composite sheets. After the plies of composite sheets are laid out, the resulting laminate is cured. After curing, the laminate is checked for defects, such as disbonds (i.e., regions in which two adjacent plies do not bond together resulting in a void) and inclusions (i.e., regions in which foreign object debris is between two adjacent plies). To correct such defects, the region with the defect is scarfed out to remove the defect and a patch of plies is installed in the scarfed out area. The patch is then cured and the rechecked for any additional defects. Such a repair procedure can be expensive and time consuming.

Figure 1A:
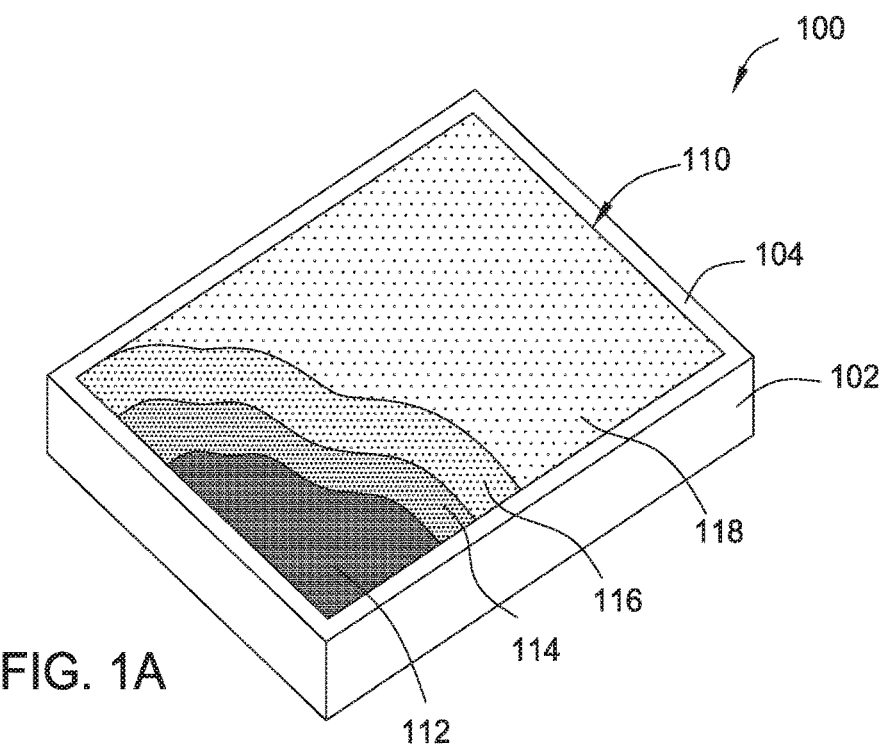
FIG. 1A is a perspective view of a layup table with four plies of composite sheets of a laminate laid out on a surface of the table, wherein three of the four plies are shown partially cut away to display the underlying plies.

FIG. 1A is a perspective view of a layup table 102 with a laminate 110 that includes four plies of composite sheets 112, 114, 116, and 118 arranged on a work surface 104 of the layup table 102. The top three plies of composite sheets 114, 116, and 118 are shown in partial cutaway to illustrate the underlying plies. The four plies are arranged in alternating directions. The first ply 112 includes fibers (e.g., carbon fibers) arranged in a first direction, the second ply 114 includes fibers arranged in a second direction that is orthogonal to the first direction, the third ply 116 includes fibers arranged in the first direction, and the fourth play includes fibers arranged in the second direction. In practice, a person or a machine would lay the first ply 112 on the work surface 104 of the layup table 102 with the fibers of the first ply 112 arranged in the first direction. The person or machine would then lay the second ply 114 on the first ply 112 with the fibers of the second ply 114 arranged in the second direction. The person or machine would then lay the third play 116 on the second ply 114 with the fibers of the third ply 116 arranged in the first direction. The person or machine would then lay the fourth ply 118 on the third ply 116 with the fibers of the fourth ply 118 arranged in the second direction. After the plies 112, 114, 116, and 118 have been laid on the work surface 104, the plies 112, 114, 116, and 118 can be compacted using rollers or the like. In various circumstances, additional plies could be laid on top of the illustrated four plies 112, 114, 116, and 118 and compacted. Also, in various circumstances, the number of plies that are laid down before a compaction step can be more or fewer than the illustrated four plies.

Figure 1B:
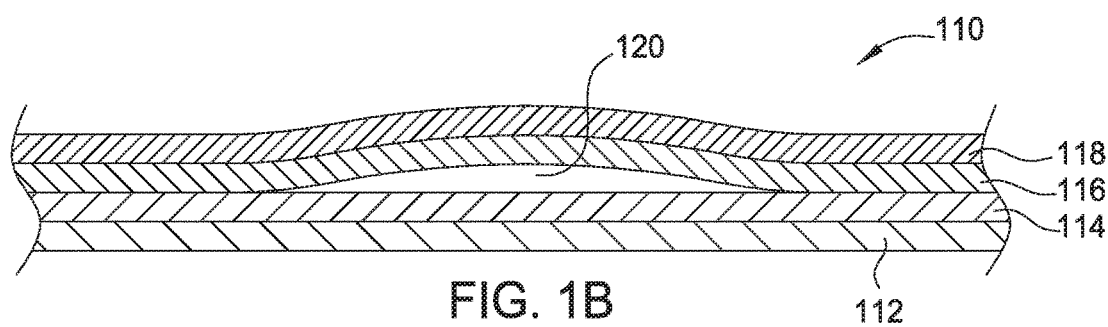
FIG. 1B is a cross-sectional side view of the four plies of the laminate of FIG. 1A with a disbond between the second and third plies.
Figure 1C:
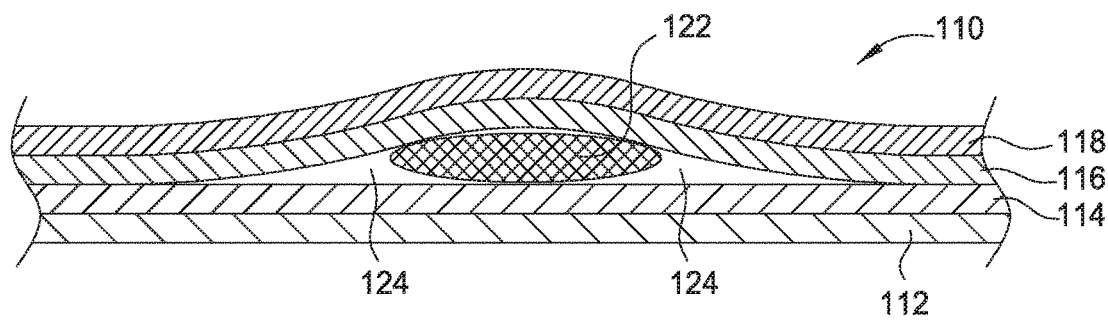
FIG. 1C is a cross-sectional side view of the four plies of the laminate of FIG. 1A with an inclusion between the second and third plies.

After compaction, it is possible for defects to exist in the uncured, compacted composite sheets. FIG. 1B illustrates an example of a disbond 120. As shown in FIG. 1B, the disbond 120 is formed where the second ply 114 and the third ply 116 were not compacted together. If a disbond 120 occurs, then the second ply 114 and the third ply 116 will not adhere to one another during a subsequent curing process. FIG. 1C illustrates an example of an inclusion 122, in which a foreign object is arranged between plies. As shown in FIG. 1C, the inclusion 122 is between the second ply 114 and the third ply 116. The inclusion could be a piece of backing paper for the second ply 114 or the third play 116 that was not removed, for example. The inclusion 122 can form disbonds 124 along edges of the inclusion 122 where the inclusion 122 prevents the adjacent plies (e.g., plies 114 and 116) from joining together. If the inclusion 122 is not removed, then the second ply 114 and the third ply 116 will not adhere to one another during the subsequent curing process. In various instances, the inclusion could be a conductive inclusion, which means that the inclusion transfers heat at a faster rate than the plies 112, 114, 116, and 118 of the laminate 110. For example, a conductive inclusion could be a metallic particle, such as a metal foil. In various other instances, the inclusion could be an insulative inclusion, which means that the inclusion transfers heat at a slower rate than the plies 112, 114, 116, and 118 of the laminate 110. For example, an insulative inclusion could be a piece of backing paper. In various instances, the inclusion could be a neutral inclusion, which means that the inclusion transfers heat at the same rate as the plies 112, 114, 116, and 118 of the laminate 110. For example, a neutral inclusion could be a piece of another ply.

Laminates, such as the laminate 110 shown in FIGS. 1A-1C, are currently inspected after the curing process using ultrasound. If a defect is found, the region of the cured laminate is scarfed out to remove the defect. Typically, the scarfed out region has a diameter of at least twenty times the size of the defect. Thus, a defect that is 0.1 centimeters across would be repaired with a scarfed out region having a diameter of two centimeters, for example. After the defect has been scarfed out of the cured laminate, a patch of uncured composite sheets is fit into the scarfed out region, compacted, and then cured in place. The repaired area is then inspected again to check for additional defects. Such a repair process is time consuming, especially if multiple defects are found in a laminate.

Figure 2:
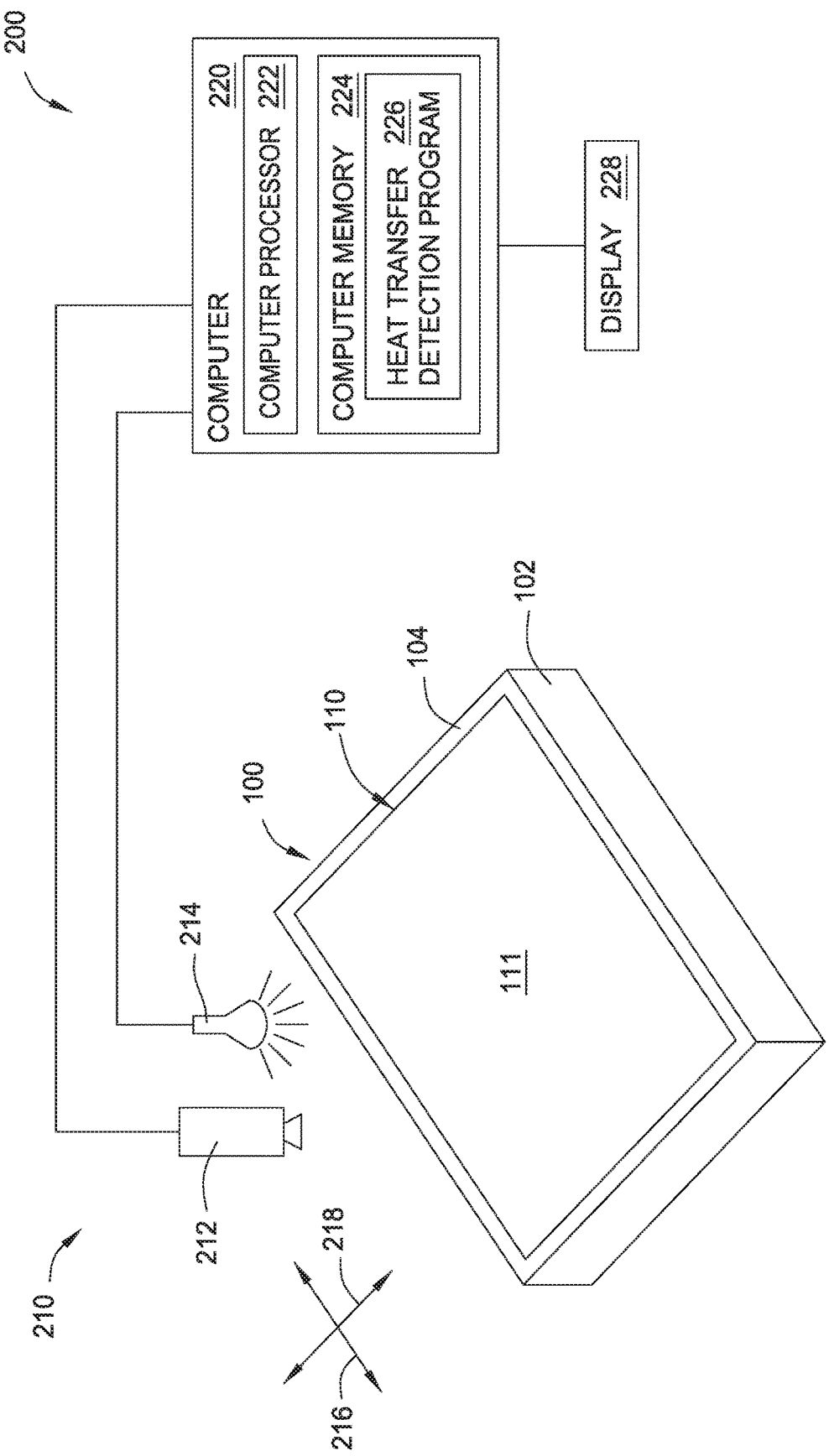
FIG. 2 is a block diagram of a system for detecting defects in a laminate of uncured, compacted composite sheets, wherein the system is shown detecting defects in the laminate shown in FIG. 1A as an exemplary scenario.

FIG. 2 illustrates a system 200 for detecting defects in a laminate, such as disbonds and inclusions, before the laminate is cured. For purposes of illustration, the system 200 is described with reference to the laminate 110 discussed above with reference to FIGS. 1A-1C. However, the system 200 could be used on other laminates. If a defect is detected prior to the laminate 110 being cured, the defect can be repaired faster and cheaper. For example, a region that includes a detected disbond could be compacted again to remove the disbond. As another example, the plies could be separated in a region that includes a detected inclusion to remove the inclusion. The plies could then be put back in place and compacted again. Such repairs could be performed more quickly and less expensively than repairs after the laminate 110 is cured.

The system 200 includes a heat source 214, such as a heat lamp or a heat gun. The heat source 214 applies a burst of heat (i.e., a momentary heat load) to a top surface 111 of the laminate 110 to increase the temperature of the top surface 111 of the laminate 110 by a small amount. For the laminate 110 described in greater detail above, the heat source 214 would apply to the top-facing surface of the fourth ply 118. For example, the heat source 214 may apply heat to the top surface 111 of the laminate 110 to increase the temperature of the top surface 111 by a few degrees or less. In any case, the heat source 214 does not apply enough heat to cause the laminate 110 to begin to cure. Depending on the size of the laminate 110, the heat source 214 could be an array of heat sources arranged over the laminate 110 to provide uniform heat application to the top surface 111 of the laminate 110. As described in greater detail below, in various aspects, the heat source 214 could be movable in the directions of arrows 216 and 218 to apply heat to different locations along the top surface 111 of the laminate 110.

The system also includes a digital thermographic camera 212 that captures images of thermal properties (e.g., temperature) and changes to the thermal properties of the top surface 111 of the laminate 110 after the heat source 214 applies the momentary heat load. For example, the digital thermographic camera 212 could be an infrared camera. After heat is applied to the top surface 111 of the laminate 110 by the heat source 214, the heat travels from the top surface 111 through the laminate 110. The rate of heat transfer from the top surface 111 to internal layers of the laminate 110 is affected by defects, such as the disbonds and inclusions discussed above with reference to FIGS. 1B and 1C, which obstruct the flow of heat from the top surface 111 into the laminate 110. By capturing successive images of heat characteristics of the top surface 111 of the laminate 110 after the application of heat by the heat source 214, disbonds and inclusions (and other flaws) can be discovered. For example, the heat characteristics of the top surface 111 could be temperatures of the surface at different regions and/or different times, a first derivative of the temperature (i.e., rate of change of the temperature of the top surface 111) and/or a second derivative of the temperature (i.e., rate of change of the rate of change of the temperature of the top surface 111). In various aspects, the digital thermographic camera 212 could be movable in the directions of arrows 216 and 218. In certain aspects, the digital thermographic camera 212 and the heat source 214 move in the directions of arrows 216 and 218 together.

The heat source 214 and thermographic camera 212 are in communication with a computer 220. The computer 220 includes a computer processor 222 and computer memory 224. The digital thermographic camera 212 can transmit captured images of thermal properties of the top surface 111 of the laminate 110 to the computer 220 for storage on the computer memory 224. In operation, the computer processor 222 sends control signals to the heat source 214 to trigger the momentary heat output to the top surface 111 of the laminate 110. The computer processor 222 also sends control signals to the digital thermographic camera 212 to trigger the digital thermographic camera 212 to capture images of thermal properties of the top surface 111 laminate 110. The computer 220 can control movement of the heat source 214 and/or the digital thermographic camera 212 in the directions of arrows 216 and 218.

The computer memory 224 can also store a heat transfer detection program 226 that, when executed by the computer processor 222, triggers the digital thermographic camera 212 and the heat source 214 and processes the stored images of thermal properties of the top surface 111 of the laminate 110. The heat transfer detection program 226 can determine heat characteristics at the different locations of the top surface 111 of the laminate 110. The heat characteristics include at least one of temperatures at different locations of the top surface 111 of the laminate 110, a rate of change of temperatures (first derivative of temperature) at the different locations of the top surface 111 of the laminate 110, and a rate of change of the rate of change of temperatures (second derivative of temperature) at the different locations of the top surface 111 of laminate 110. The temperature, first derivative of temperature, and/or second derivative of temperature for the top surface 111 of the laminate 110 can be determined over a period of time to identify regions of the top surface 111 of the laminate 110 that have different heat transfer properties from the remainder of the laminate 110. As discussed, disbonds and/or inclusions (and other defects) in the laminate 110 can change the rate of heat transfer relative to regions of the laminate 110 that do not include such defects. For a typical laminate (e.g., laminate 110) that may have only a few defects, the majority of the top surface of the laminate will have the same or very similar heat characteristics. The regions of the laminate that include defects will have different heat characteristics. By identifying regions of the laminate 110 where the heat characteristics of the top surface 111 differ from other regions, the locations of defects can be identified.

The system 200 can include a display 228 in communication with the computer 220. In the event a defect is detected in the laminate 110 by the computer 220, the display 228 could output an alert or alarm. The display 228 and could provide an indication of a location of the laminate 110 that includes the defect. For example, the display 228 could be a computer display screen that flashes to indicate a detected defect and that provides coordinates and/or a graphical depiction of a location of the defect on the laminate 110.

Figure 3:
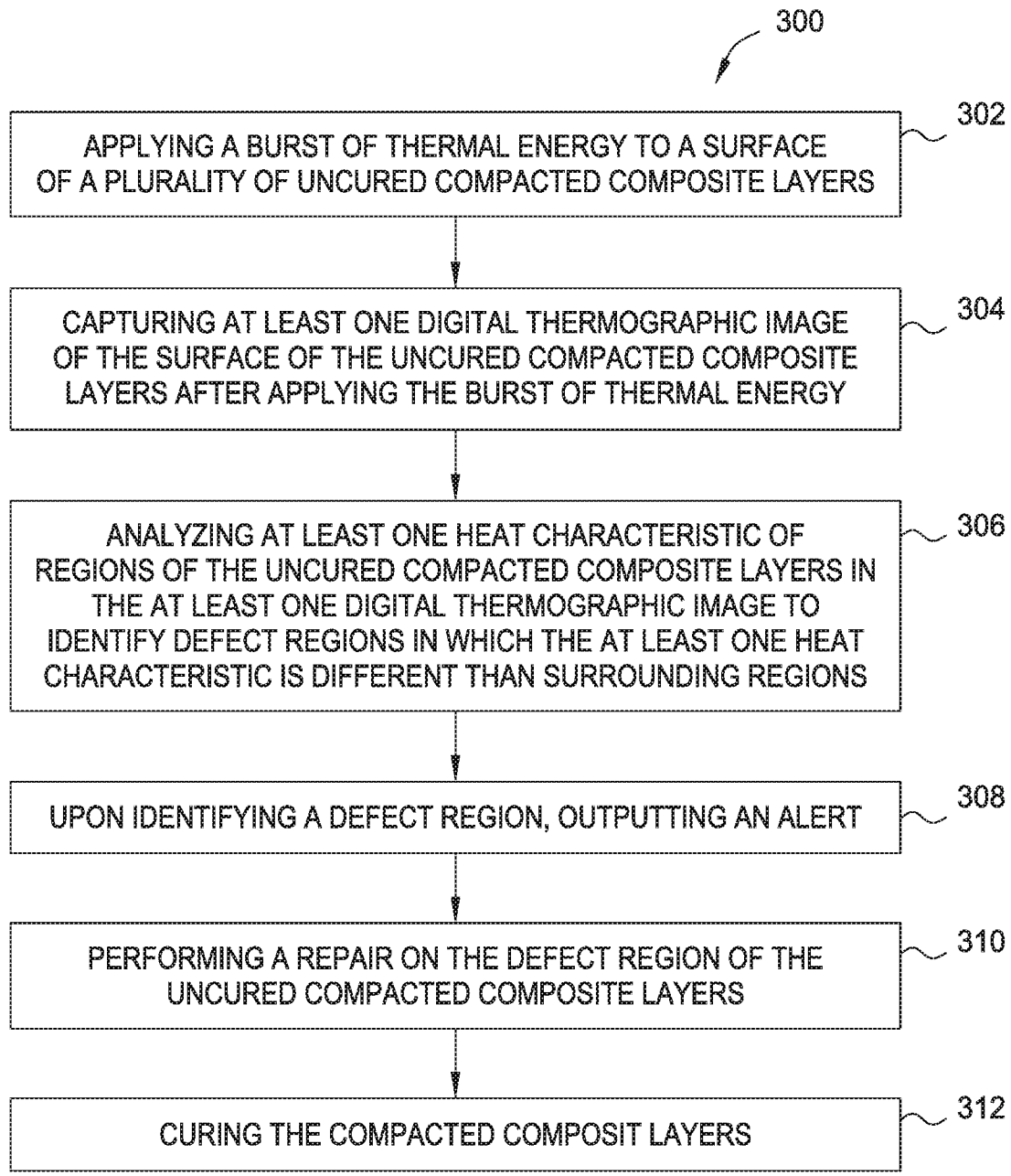
FIG. 3 is a flow chart of a process for detecting a defect in a laminate of uncured, compacted composite sheets.

FIG. 3 is a flowchart for a process 300 for detecting and correcting defects in a laminate (e.g., the laminate 110) prior to curing the laminate. In block 302, a burst of thermal energy is applied to a surface of a plurality of uncured compacted composite layers (e.g., the composite sheets 112, 114, 116, and 118 shown in FIGS. 1A-1C). As discussed above, the burst of thermal energy can be applied by the heat source 214 of the system 200, shown in FIG. 2. In block 304, at least one digital thermographic image of the surface of the uncured compacted composite layers is captured. As discussed above, the least one digital thermographic image captured by the digital thermographic camera 212 of the system 200, shown in FIG. 2. In block 306, the at least one digital thermographic image can be analyzed to identify at least one heat characteristic of regions of the uncured compacted composite layers to identify defect regions in which the at least one heat characteristic is different than surrounding regions. As discussed above, the heat transfer detection program 226 executing on the computer processor 222 of the system could analyze the at least one digital thermographic image stored in computer memory 224 to identify at least one heat characteristic, which could be a temperature over time, a first derivative of temperature over time, and/or a second derivative of temperature over time of the top surface 111 of the laminate 110. In block 308, upon identifying a defect region, and alarm or alert is output. As discussed above, the display 228 of the system 200 could display such an alarm or alert. In block 310, a repair is performed on the defect region of the uncured compacted composite layers. For example, if the defect in the defect region is known to be or believed to be a disbond, then additional compaction steps could be performed to eliminate the disbond. As another example, if the defect in the defect region is known to be or believed to be an inclusion, then layers of the laminate 110 can be at least partially removed to reveal the inclusion, the inclusion could be removed, and the layers could be replaced. Thereafter, an additional compaction procedure could be performed to re-compact the layers that had been removed. In block 312, after detected defects have been repaired, the laminate 110 can be cured.

Figure 4:
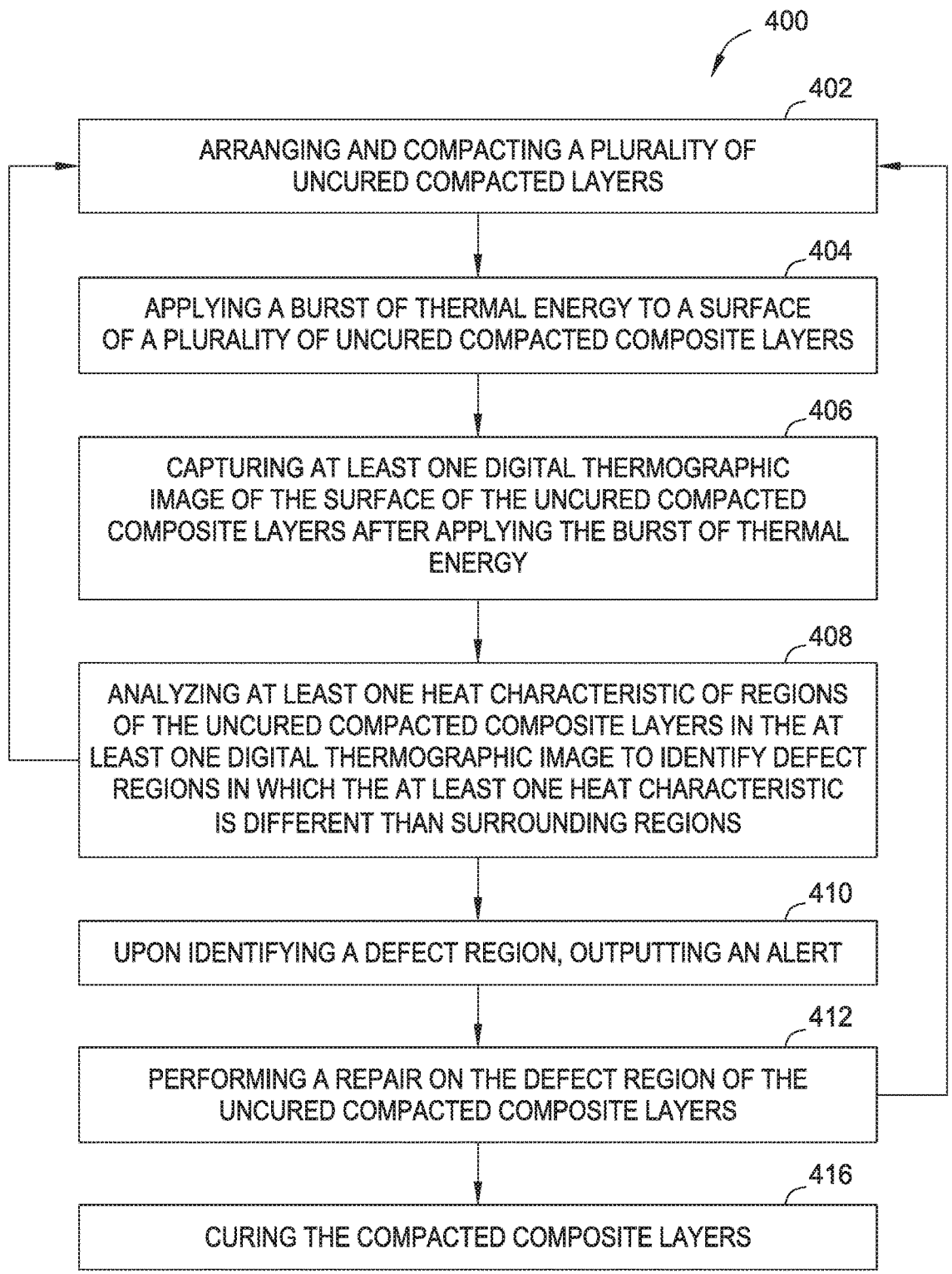
FIG. 4 is a flow chart of a process for building a laminate of compacted composite sheets.

FIG. 4 is a flowchart for a process 404 assembling a laminate that includes a plurality of layers. In block 402, a plurality of uncured composite layers are arranged and compacted. In block 404, a burst of thermal energy is applied to a surface of a plurality of uncured compacted composite layers (e.g., the composite sheets 112, 114, 116, and 118 shown in FIGS. 1A-1C). As discussed above, the burst of thermal energy can be applied by the heat source 214, shown in FIG. 2. In block 406, at least one digital thermographic image of the surface of the uncured compacted composite layers is captured. As discussed above, the least one digital thermographic image captured by the digital thermographic camera 212, shown in FIG. 2. In block 408, the at least one digital thermographic image can be analyzed to identify at least one heat characteristic of regions of the uncured compacted composite layers to identify defect regions in which the at least one heat characteristic is different than surrounding regions. As discussed above, the at least one heat characteristic could be a temperature over time, a first derivative of temperature over time, and/or a second derivative of temperature over time of the top surface 111 of the laminate 110. In the event no defects are found, then the process 400 could return to block 402, if necessary, to arrange and compact additional uncured composite layers on the laminate. Blocks 402, 404, 406, and 408 could be repeated until the laminate includes a suitable number of uncured composite layers. The number of uncured composite layers added with each iteration of blocks 402, 404, 406, and 408 of the process 400 can vary depending on various circumstances. In some circumstances, as few as one or two layers may be added with each iteration through blocks 402, 404, 406, and 408. In other circumstances, as many as four, five, or more uncured composite layers could be added with each iteration through blocks 402, 404, 406, and 408. As discussed in greater detail below, certain heat sources and digital thermographic cameras may have sufficient sensitivity to detect defects that are three, four, or more layers deep in a laminate of uncured, compacted composite layers whereas other heat sources and digital thermographic cameras may be limited to detecting defects that are one or two layers deep. Thus, the number of layers added with each iteration through blocks 402, 404, 406, and 408 could be dependent on the type of heat source and/or digital thermographic camera used in blocks 404 and 406.

In at least one aspect, blocks 402, 404, 406, and 408 could be performed in a continuous manner. For example, in at least one aspect, the laminate could be applied around a cylindrical mandrel by wrapping a continuous composite sheet around the mandrel. As the continuous composite sheet is laid on the mandrel (and on top of portions of the continuous sheet that have already been laid on the mandrel), the composite sheet is compacted (e.g., by a roller). The heat source and digital thermographic camera could follow behind the compacting apparatus to analyze the compacted uncured laminate for defects.

In block 410, upon identifying a defect region, and alarm or alert is output. In block 412, a repair is performed on the defect region of the uncured compacted composite layers. For example, if the defect in the defect region is known to be or is most likely a disbond, then additional compaction steps could be performed to eliminate the disbond. As another example, if the defect in the defect region is known to be or is most likely an inclusion, then layers of the laminate 110 can be removed to reveal the inclusion, the inclusion could be removed, and the layers could be replaced. Thereafter, additional compaction procedure could be performed to re-compact the layers that had been removed. After the defects have been removed, the process 400 can optionally return to block 402 to arrange and compact additional uncured composite layers.

In block 416, after all of the uncured composite layers have been arranged in compacted and any detected defects have been repaired, the laminate 110 can be cured.

Figure 5A:
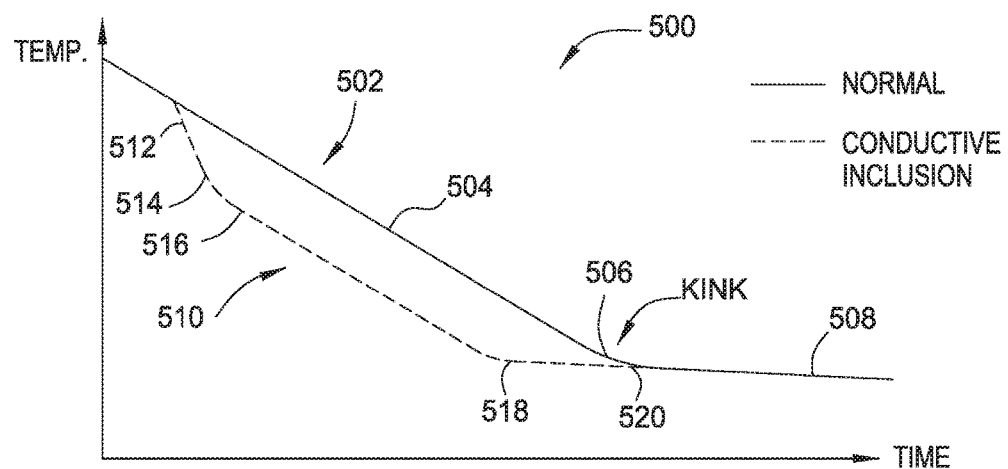
FIG. 5A is a chart illustrating a temperature response over time for a defect-free laminate of uncured, compacted composite sheets and a laminate of uncured, compacted composite sheets having a conductive inclusion.
Figure 5B:
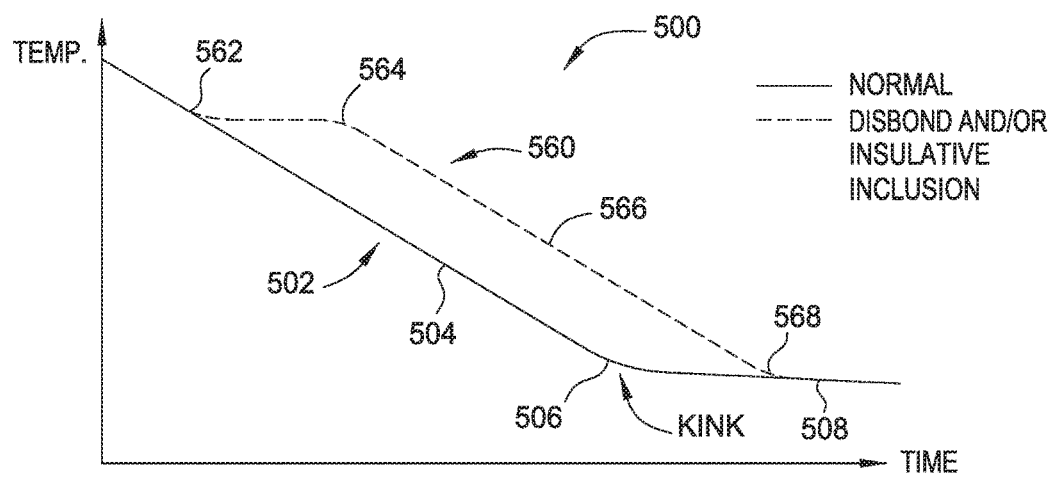
FIG. 5B is a chart illustrating a temperature response over time for a defect-free laminate of uncured, compacted composite sheets and a laminate of uncured, compacted composite sheets having a disbond and/or an inclusion.

FIGS. 5A-5B illustrate temperature profiles that may be detected by a digital thermographic camera, such as the digital thermographic camera 212 shown in FIG. 2. FIG. 5A illustrates the differences in temperature of the top surface 111 of the laminate 110 over time for a defect-free region of the laminate and a region that has a conductive inclusion. As explained above, a conductive inclusion is an inclusion (e.g., debris) that conducts heat more readily than the laminate layers. For example, a piece of metal caught between layers of the laminate could be a conductive inclusion. After a heat source, such as the heat source 214 shown in FIG. 2, outputs a burst of energy directed toward the top surface 111 of the laminate 110, the temperature of the top surface 111 of the laminate 110 rises. The chart 500 in FIG. 5A includes a solid line 502 indicating the normal (i.e., defect free) region of the laminate and a broken line 510 indicating the region that has a conductive inclusion. The left-hand ends of the solid line 502 and the broken line 510 indicate the temperature of the top surface 111 of the laminate 110 immediately after the burst of energy from the heat source 214 is applied to the top surface 111. Energy absorbed by the top surface 111 has caused the temperature of the top surface 111 to increase. After the initial increase in temperature of the top surface 111, the temperature of the top surface 111 begins to decrease in a linear manner as the heat energy applied to the top surface 111 travels deeper into the laminate via conduction (as indicated by first portion 504 of the solid line 502). The initial rate of heat transfer away from the top surface 111 via conduction is substantially the same for both the normal region and the region that includes the inclusion, as indicated by the initial overlap of the solid line 502 and the broken line 510.

Referring to the normal region, indicated by the solid line 502, as the heat energy reaches a bottom side of the laminate 110, the heat energy can travel no further through the laminate via conductance. Thereafter, the heat transfer away from the top surface 111 slows, as indicated by the kink 506 and the reduced-slope second portion 508 of the solid line 502.

Referring to the conductive inclusion region, indicated by the broken line 510, before the heat energy reaches the bottom side of the laminate 110, the heat energy encounters the conductive inclusion (e.g., the inclusion 122 shown in FIG. 1C could be a conductive inclusion). The exemplary conductive inclusion provides additional mass that can act as a heat sink for the laminate such that heat from the top surface 111 can be transferred to the inclusion via conductance. Furthermore, because the exemplary conductive inclusion is more conductive than the surrounding layers of laminate, the top surface 111 of the laminate 110 over the conductive inclusion cools faster than surrounding regions of the top surface 111. This faster cooling of the top surface 111 is indicated by a first kink 512 of the broken line 510 as the broken line 510 deviates from the solid line 502. As the conductive inclusion warms, the heat transfer from the top surface 111 slows, and the broken line 510 has a second kink 514. After the second kink 514, the rate of temperature change of the top surface 111 over the conductive inclusion is substantially equal to the rate of temperature change of the top surface 111 over normal regions of the laminate 110, as indicated by portion 504 of the solid line 502, as indicated by the portion 516 of the broken line 510. Because the conductive inclusion transfers heat away from the top surface 111 faster, the heat reaches the back surface of the laminate 110 at the conductive inclusion faster than at surrounding normal regions. Thereafter, the heat transfer away from the top surface 111 over the conductive inclusion slows, as indicated by the kink 518 in the broken line, which eventually joins the second portion of the solid line 502 (at the point indicated by reference numeral 520).

For a laminate that is only three, four, or five layers thick, the kinks 506 and 518 in the temperature profiles for a normal region and a region that includes a conductive inclusion may be observable in a reasonable period of time. For example, the kinks 506 and 518 may occur within three to ten seconds after heat is applied to the top surface 111 of the laminate 110. However, in instances in which the laminate is thicker (e.g., including tens of layers, such as fifty layers, one hundred layers, or one hundred and fifty layers), the kinks 506 and 518 may not be observable in a suitable period of time for such an inspection. In such instances, the kink 512 and/or the kink 514 in the temperature profile of the top surface 111 over the conductive inclusion should be perceivable. The kink 506 in the temperature profile of the top surface 111 over normal regions does not need to be observed. For example, assuming that most of the laminate 110 is free from defects, the temperature profile over time would be substantially homogenous. However, if a particular region includes a conductive inclusion, that region would have a temperature profile that decreases at a faster rate (at the kink 512) than the defect free regions. Thus, observing a temperature profile decreasing at a faster rate than surrounding regions could indicate the presence of a conductive inclusion in the laminate 110.

Figure 6A:
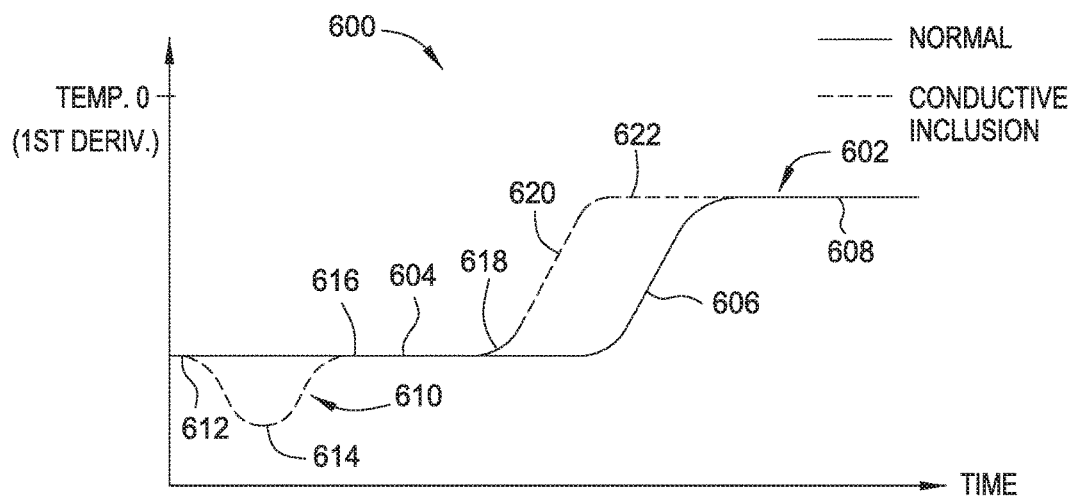
FIG. 6A is a chart illustrating a first derivative of the temperature response over time for the defect-free laminate of uncured, compacted composite sheets and the laminate of uncured, compacted composite sheets having the conductive inclusion shown in FIG. 5A.

FIG. 6A illustrates a chart 600 showing a calculated first derivative of the temperature (i.e., a rate of change of temperature) of the top surface 111 of laminate 110 for the defect free (i.e., normal) region, indicated by the solid line 602, and of the region that has the conductive inclusion, discussed above with reference to FIG. 5A, indicated by the broken line 610. As shown in FIG. 6A, the first derivative of temperature for the normal region is a first rate of change, indicated by portion 604 of the solid line 602, which corresponds with the first portion 504 of the solid line 502 in FIG. 5A. Since the temperature of the top surface 111 is decreasing, the values of the first derivative are negative. Stated differently, a zero value on the temperature axis of the chart 600 is above the illustrated solid line 602 and the broken line 610. When the temperature profile of the top surface 111 over the normal region reaches the kink 506 in FIG. 5A, the first derivative of temperature for the normal region increases (toward zero), as indicated by the portion 606 of the solid line 602. Thereafter, the first derivative of temperature for the normal region settles at a second rate of heat transfer, as indicated by the portion 608 of the solid line 602. The first derivative of temperature for the region that includes the conductive inclusion diverges from the first derivative of temperature for the normal region twice. First, where the temperature profile of the top surface 111 for the conductive inclusion decreases faster than surround normal regions at the kinks 512 and 514 (in FIG. 5A), the first derivative of temperature decreases (away from zero) from the first rate of change (indicated by the portion 604 of the solid line 602) at the point indicated by reference numeral 612, reaches a peak at the point indicated by reference numeral 614, and then increases (toward zero) at the point indicated by reference numeral 616. When the temperature profile of the top surface 111 over the conductive inclusion reaches the kink 518 in FIG. 5A, the first derivative of temperature increases (toward zero) at the point indicated by reference numeral 618 and as indicated by the portion 620 of the broken line 610. Thereafter, the first derivative of temperature for the conductive inclusion settles at the second rate of heat transfer, as indicated by the portion 622 of the broken line 610.

As discussed above, in instances in which only a few layers of laminate have been laid out, the kinks 506 and 518 of the temperature profiles for the normal regions and conductive inclusions may be perceivable in a suitable period of time for an inspection. In other instances in which many layers of laminate have been laid out, the kinks 506 and 518 may not be perceivable in a suitable period of time. Consequently, the changes of the first derivatives of temperature from the first rate of change (at portion 604) to the second rate of change (at portions 622 and 608) also would not be perceivable. However, the peak 614 of the first derivative of temperature for the conductive inclusion corresponding to the earlier kinks 512 and 514 would be perceivable relative to values of the first derivative of temperature for surrounding normal regions.

Figure 7A:
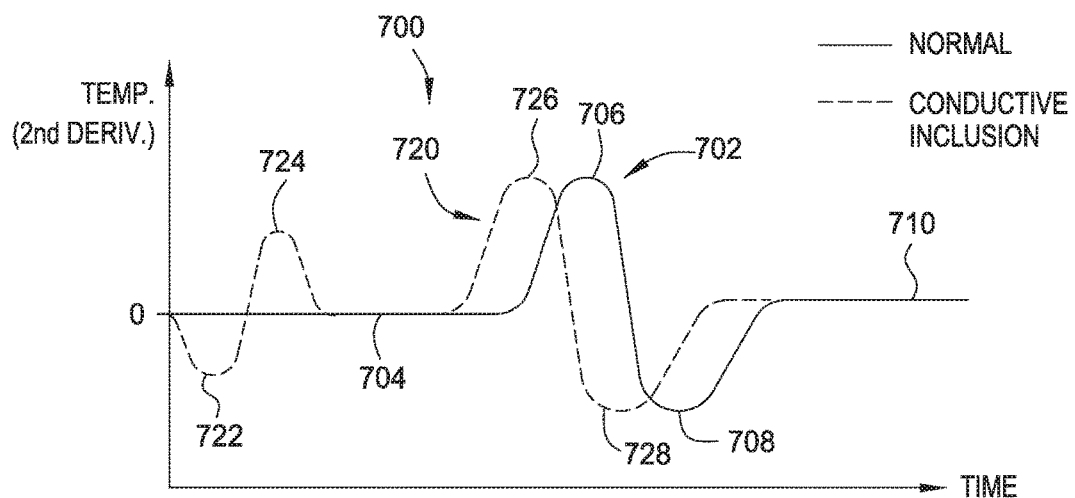
FIG. 7A is a chart illustrating a second derivative of the temperature response over time for the defect-free laminate of uncured, compacted composite sheets and the laminate of uncured, compacted composite sheets having the conductive inclusion shown in FIG. 5A.

FIG. 7A illustrates a chart 700 showing a calculated second derivative of the temperature of the top surface 111 of laminate 110 for the defect free (i.e., normal) region, indicated by the solid line 702, and to the region that has the conductive inclusion, discussed above with reference to FIG. 5A, indicated by the broken line 720. As shown in FIG. 7A, the second derivative of temperature for the normal region is zero along a first portion 704 of the solid line 702 until reaching a first peak 706 and then a second opposing peak 708 that corresponds with the kink 506 in the temperature plot shown in the chart 500 of FIG. 5A and the rate of change trending from the first rate of change indicated by the portion 604 to the portion 608 (via portion 606) of the solid line 602 in FIG. 6A. The second derivative of temperature for the region that includes the conductive inclusion results in similar peaks 726 and 728 that correspond to the kink 518 in the temperature plot of the chart 500 shown in FIG. 5A and the rate of change trending from the first rate of change indicated by the portion 604 to the portion 622 (via portion 620) of the broken line 610 in FIG. 6A. The second derivative of temperature for the region that includes the conductive inclusion also includes an additional set of peaks 722 and 724 that correspond with the kinks 512 and 514 of the temperature plot shown in FIG. 5A and the rate of change changing temporarily from the first rate of change indicated by the portion 604 of the solid line 602 to the peak 614 rate of change and then returning to the first rate of change 604.

As discussed above, in instances in which only a few layers of laminate have been laid out, the kinks 506 and 518 of the temperature profiles for the normal regions and conductive inclusions may be perceivable in a suitable period of time for an inspection. In other instances in which many layers of laminate have been laid out, the kinks 506 and 518 may not be perceivable in a suitable period of time. Consequently, the peaks 706 and 708 for the normal regions and the peaks 726 and 728 for the conductive inclusion regions, corresponding to the kinks 506 and 518, may not be perceivable in a suitable period of time. However, the peaks 722 and 724 of the second derivative of temperature for the conductive inclusion, corresponding to the earlier kinks 512 and 514, would be perceivable relative to values of the first derivative of temperature for surrounding normal regions.

FIG. 5B illustrates the differences in temperature of the top surface 111 of the laminate 110 over time for a defect-free region of the laminate and a region that has a disbond and/or an insulative inclusion. As explained above, an insulative inclusion is an inclusion (e.g., debris) that conducts heat less readily than the laminate layers. For example, a piece of backing paper caught between layers of the laminate could be an insulative inclusion. After a heat source, such as the heat source 214 shown in FIG. 2, outputs a burst of energy directed toward the top surface 111 of the laminate 110, the temperature of the top surface 111 of the laminate 110 rises. The chart 550 in FIG. 5B includes the solid line 502 indicating the normal (i.e., defect free) region of the laminate and a broken line 560 indicating the region that has a disbond and/or insulative inclusion. The left-hand ends of the solid line 502 and the broken line 560 indicate the temperature of the top surface 111 of the laminate 110 immediately after the burst of energy from the heat source 214 is applied to the top surface 111. Energy absorbed by the top surface 111 has caused the temperature of the top surface 111 to increase. After the initial increase in temperature of the top surface 111, the temperature of the top surface 111 begins to decrease in a linear manner as the heat energy applied to the top surface 111 travels deeper into the laminate via conduction (as indicated by first portion 504 of the solid line 502). The initial rate of heat transfer away from the top surface 111 via conduction is substantially the same for both the normal region and the region that includes the inclusion, as indicated by the initial overlap of the solid line 502 and the broken line 560.

Referring to the normal region, indicated by the solid line 502, as the heat energy reaches a bottom side of the laminate 110, the heat energy can travel no further through the laminate via conductance. Thereafter, the heat transfer away from the top surface 111 slows, as indicated by the kink 506 and the reduced-slope second portion 508 of the solid line 502.

Referring to the disbond and/or insulative inclusion region, indicated by the broken line 560, before the heat energy reaches the bottom side of the laminate 110, the heat energy encounters the disbond and/or insulative inclusion (e.g., the inclusion 122 shown in FIG. 1C could be an insulative inclusion). The exemplary disbond and/or insulative inclusion provides additional mass that can act as a heat sink for the laminate such that heat from the top surface 111 can be transferred to the inclusion via conductance. However, because the exemplary disbond and/or insulative inclusion is less conductive than the surrounding layers of laminate, the top surface 111 of the laminate 110 over the disbond and/or insulative inclusion cools slower than surrounding regions of the top surface 111. This slower cooling of the top surface 111 is indicated by a first kink 562 of the broken line 560 as the broken line 560 deviates from the solid line 502. Over time, the heat transfer from the top surface 111 increases and the broken line 560 has a second kink 564. After the second kink 564, the rate of temperature change of the top surface 111 over the disbond and/or insulative inclusion is substantially equal to the rate of temperature change of the top surface 111 over normal regions of the laminate 110, as indicated by portion 504 of the solid line 502, as indicated by the portion 566 of the broken line 560. Because the disbond and/or insulative inclusion transfers heat away from the top surface 111 slowly, the heat reaches the back surface of the laminate 110 at the disbond and/or insulative inclusion slower than at surrounding normal regions. Thereafter, the heat transfer away from the top surface 111 over the disbond and/or insulative inclusion slows, as indicated by the kink 568 in the broken line, and eventually joins the second portion of the solid line 502.

For a laminate that is only three, four, or five layers thick, the kinks 506 and 568 in the temperature profiles for a normal region and a region that includes a disbond and/or insulative inclusion may be observable in a reasonable period of time. For example, the kinks 506 and 568 may occur within three to ten seconds after heat is applied to the top surface 111 of the laminate 110. However, in instances in which the laminate is thicker (e.g., including tens of layers, such as fifty layers, one hundred layers, or one hundred and fifty layers), the kinks 506 and 568 may not be observable in a suitable period of time for such an inspection. In such instances, the kink 562 and/or the kink 564 in the temperature profile of the top surface 111 over the disbond and/or insulative inclusion should be perceivable in a suitable period of time. The kink 506 in the temperature profile of the top surface 111 over normal regions does not need to be observed. For example, assuming that most of the laminate 110 is free from defects, the temperature profile over time would be substantially homogenous. However, if a particular region includes a disbond and/or insulative inclusion, that region would have a temperature profile that decreases at a slower rate (at the kink 562) than the defect free regions. Thus, observing a temperature profile decreasing at a slower rate than surrounding regions could indicate the presence of a disbond and/or insulative inclusion in the laminate 110.

Figure 6B:
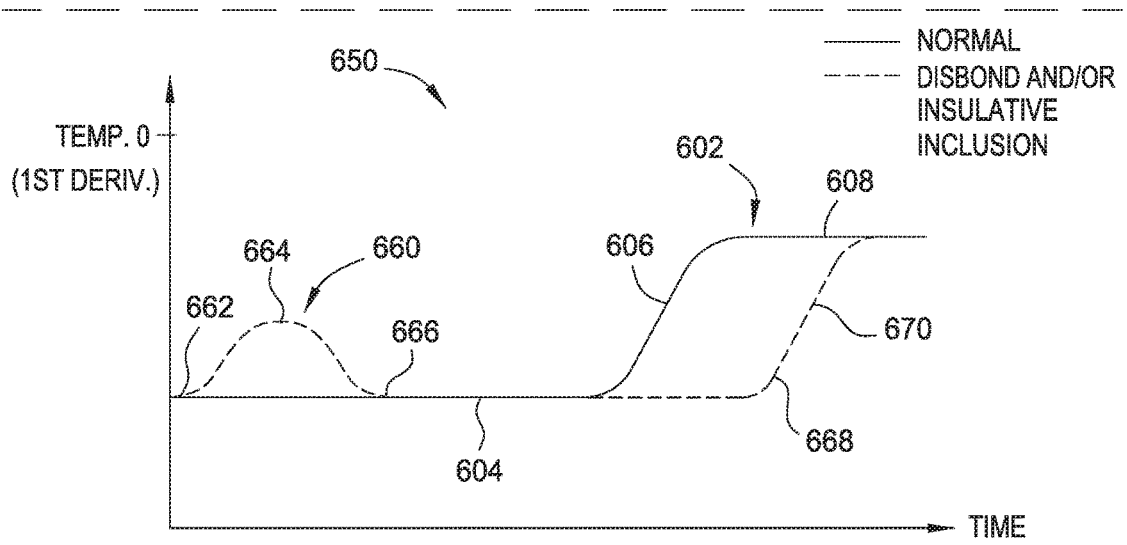
FIG. 6B is a chart illustrating a first derivative temperature response over time for the defect-free laminate of uncured, compacted composite sheets and the laminate of uncured, compacted composite sheets having the disbond and/or insulative inclusion shown in FIG. 5B.

FIG. 6B illustrates a chart 650 showing a calculated first derivative of the temperature (i.e., a rate of change of temperature) of the top surface 111 of laminate 110 for the defect free (i.e., normal) region, indicated by the solid line 602, and of the region that has the disbond and/or insulative inclusion, discussed above with reference to FIG. 5B, indicated by the broken line 660. As shown in FIG. 6B, the first derivative of temperature for the normal region is a first rate of change, indicated by portion 604 of the solid line 602, which corresponds with the first portion 504 of the solid line 502 in FIG. 5B. Since the temperature of the top surface 111 is decreasing, the values of the first derivative are negative. Stated differently, a zero value on the temperature axis of the chart 650 is above the illustrated solid line 602 and the broken line 610. When the temperature profile of the top surface 111 over the normal region reaches the kink 506 in FIG. 5B, the first derivative of temperature for the normal region increases (toward zero), as indicated by the portion 606 of the solid line 602. Thereafter, the first derivative of temperature for the normal region settles at a second rate of heat transfer, as indicated by the portion 608 of the solid line 602. The first derivative of temperature for the region that includes the disbond and/or insulative inclusion diverges from the first derivative of temperature for the normal region twice. First, where the temperature profile of the top surface 111 for the disbond and/or insulative inclusion decreases slower than surround normal regions at the kinks 562 and 564 (in FIG. 5B), the first derivative of temperature increases (toward zero) from the first rate of change (indicated by the portion 604 of the solid line 602) at the point indicated by reference numeral 662, reaches a peak at the point indicated by reference numeral 664, and then decreases (away from zero) at the point indicated by reference numeral 666. When the temperature profile of the top surface 111 over the disbond and/or insulative inclusion reaches the kink 568 in FIG. 5B, the first derivative of temperature increases (toward zero) at the point indicated by reference numeral 668 and as indicated by the portion 670 of the broken line 660. Thereafter, the first derivative of temperature for the disbond and/or insulative inclusion settles at the second rate of heat transfer, as indicated by the portion 608 of the solid line 602.

As discussed above, in instances in which only a few layers of laminate have been laid out, the kinks 506 and 568 of the temperature profiles for the normal regions and disbond and/or insulative inclusions may be perceivable in a suitable period of time for an inspection. In other instances in which many layers of laminate have been laid out, the kinks 506 and 568 may not be perceivable in a suitable period of time. Consequently, the changes of the first derivatives of temperature from the first rate of change (at portion 604) to the second rate of change (at portion 608) also would not be perceivable. However, the peak 664 of the first derivative of temperature for the disbond and/or insulative inclusion corresponding to the earlier kinks 562 and 564 would be perceivable relative to values of the first derivative of temperature for surrounding normal regions.

Figure 7B:
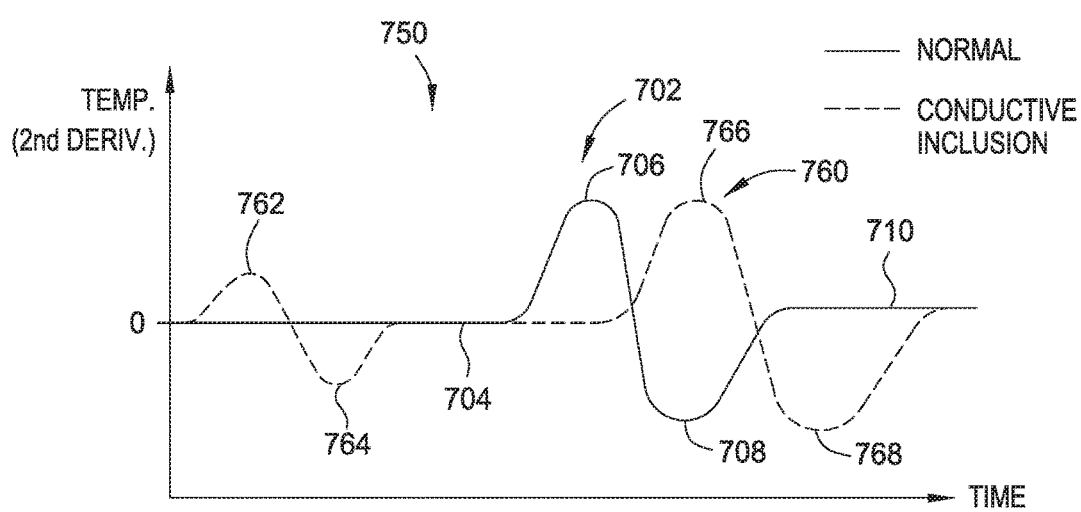
FIG. 7B is a chart illustrating a second derivative temperature response over time for the defect-free laminate of uncured, compacted composite sheets and the laminate of uncured, compacted composite sheets having the disbond and/or insulative inclusion shown in FIG. 5B.

FIG. 7B illustrates a chart 750 showing a calculated second derivative of the temperature of the top surface 111 of laminate 110 for the defect free (i.e., normal) region, indicated by the solid line 702, and to the region that has the disbond and/or insulative inclusion, discussed above with reference to FIG. 5B, indicated by the broken line 760. As shown in FIG. 7B, the second derivative of temperature for the normal region is zero along a first portion 704 of the solid line 702 until reaching a first peak 706 and then a second opposing peak 708 that corresponds with the kink 506 in the temperature plot shown in the chart 550 of FIG. 5B and the rate of change trending from the first rate of change indicated by the portion 604 to the portion 608 (via portion 606) of the solid line 602 in FIG. 6B. The second derivative of temperature for the region that includes the disbond and/or insulative inclusion results in similar peaks 766 and 768 that correspond to the kink 568 in the temperature plot of the chart 550 shown in FIG. 5B and the rate of change trending from the first rate of change indicated by the portion 604 to the portion 622 (via portion 620) of the broken line 660 in FIG. 6B. The second derivative of temperature for the region that includes the disbond and/or insulative inclusion also includes an additional set of peaks 762 and 764 that correspond with the kinks 562 and 564 of the temperature plot shown in FIG. 5B and the rate of change changing temporarily from the first rate of change indicated by the portion 604 of the solid line 602 to the peak 664 rate of change and then returning to the first rate of change of the solid line 604.

As discussed above, in instances in which only a few layers of laminate have been laid out, the kinks 506 and 568 of the temperature profiles for the normal regions and disbond and/or insulative inclusions may be perceivable in a suitable period of time for an inspection. In other instances in which many layers of laminate have been laid out, the kinks 506 and 568 may not be perceivable in a suitable period of time. Consequently, the peaks 706 and 708 for the normal regions and the peaks 766 and 768 for the disbond and/or insulative inclusion regions, corresponding to the kinks 506 and 568, may not be perceivable in a suitable period of time. However, the peaks 762 and 764 of the second derivative of temperature for the disbond and/or insulative inclusion, corresponding to the earlier kinks 562 and 564, would be perceivable relative to values of the first derivative of temperature for surrounding normal regions.

In instances in which the laminate 110 includes a neutral inclusion (e.g., an inclusion with the same heat transfer characteristics as the plies of the laminate, such as a scrap of another ply), such a neutral inclusion may be detectable if it occurs in the first several layers of a laminate. Such a neutral inclusion may include disbonds surrounding it. For example, the inclusion 122 shown in FIG. 1C includes disbonds 124 (i.e., voids or air gaps) in regions immediately surrounding the inclusion. Such disbonds 124 may be detectable as discussed above with reference to FIGS. 5B, 6B, and 7B.

Referring again to FIG. 2, in use, the heat transfer detection program 226 executing on the computer processor 222 could evaluate the temperature, first derivative of temperature, and/or second derivative of temperature for every pixel of every image stored in memory 224 from the digital thermographic camera 212. Pixels or regions of pixels that have different heat characteristics then surrounding pixels or regions could be identified as regions containing defects, and the defects could be addressed, as discussed above with reference to FIGS. 3 and 4. In aspects of the system 200 in which the digital thermographic camera 212 has a view of the entire laminate 110, each pixel of a digital thermographic image captured by the digital thermographic camera 212 corresponds to a particular region of the laminate 110. Thus, defects in the laminate 110, detected in pixels or regions of pixels in the digital thermographic images, can be located by finding the location(s) on the laminate 110 corresponding to the pixels that indicate the defect(s).

In various aspects of the system, the digital thermographic camera 212 may not capture an image of the entire laminate 110. In such aspects, the digital thermographic camera 212 and the heat source 214 may move in the directions of arrows 216 and/or 218 to capture images of different portions of the laminate 110. At least one aspect, the digital thermographic camera 212 and heat source 214 could continuously move while the heat source 214 applies heat to the top surface 111 of laminate 110 and the digital thermographic camera 212 captures digital thermographic images of the temperature of the top surface 111 of the laminate 110. In such aspects, the system 200 could map the pixels of the image to locations on the laminate 110 as described in U.S. application Ser. No. 14/614,198, filed on Feb. 16, 2015, and entitled "system and method for high-speed FOD detection," the entire contents of which are incorporated by reference herein.

The system 200 could include one of several different combinations of digital thermographic camera 212 and heat source 214. For example, the digital thermographic camera 212 and heat source 214 could be included in a single unit such as the Thermoscope® II manufactured by Thermal Wave Imaging. In at least one test, a similar thermal wave imaging system was able to detect an inclusion under two or three layers of uncured compacted composite sheets. As another example, the VoyageIR® 2 thermal processing system by Thermal Wave Imaging combines the digital thermographic camera 212 and heat source 214 into a single unit and, in at least one test, was able to detect an inclusion under two or three layers of uncured compacted composite sheets. As another example, a ThermaCam™ SC640 infrared camera by FLIR Systems® could be used as the digital thermographic camera 212, and could be used in combination with a heat source 212, such as a heat gun or lamp. In at least one test, such an infrared camera was able to detect an inclusion under one layer of uncured compacted composite sheet. As yet another example, an E40 infrared camera by FLIR Systems® could be used as the digital thermographic camera 212, and could be used in combination with a heat source 212, such as a heat gun or lamp. In at least one test, such an infrared camera was able to detect an inclusion under one layer of uncured compacted composite sheet.

The descriptions of the various aspects have been presented for purposes of illustration, but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects disclosed herein.

Aspects described herein may take the form of an entirely hardware aspect, an entirely software aspect (including firmware, resident software, micro-code, etc.) or an aspect combining software and hardware aspects that may all generally be referred to herein as a "circuit," "module" or "system."

Aspects described herein may be a system, a method, and/or a computer program product. The computer program product may include a computer readable storage medium (or media) having computer readable program instructions thereon for causing a processor to carry out aspects described herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations described herein may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some aspects, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects described herein.

Aspects are described herein with reference to flowchart illustrations and/or block diagrams of methods, apparatus (systems), and computer program products according to aspects. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects described herein. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Aspects described herein may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of at least one aspect, a user may access applications (e.g., the heat transfer detection program 226) or related data available in the cloud. For example, the heat transfer detection program 226 could execute on a computing system in the cloud and detect defects, such as disbonds and/or inclusions in uncured compacted layers of composite sheets. In such a case, the heat transfer detection program 226 could analyze images captured by the digital thermographic camera 212 and store the analysis of the images at a storage location in the cloud. Doing so allows a user to access this information from any computing system attached to a network connected to the cloud (e.g., the Internet).

While the foregoing is directed to certain aspects, other and further aspects may be devised without departing from the basic scope thereof, and the scope thereof is determined by the claims that follow.

What is claimed is:

1. A method, comprising:
   applying a burst of thermal energy to a surface of a plurality of uncured compacted composite layers;
   capturing at least one digital thermographic image of the surface of the uncured compacted composite layers after applying the burst of thermal energy;
   using a computer processor, analyzing at least one heat characteristic of regions of the uncured compacted composite layers in the at least one digital thermographic image to identify defect regions in which the at least one heat characteristic is different than surrounding regions, wherein the at least one heat characteristic of the uncured compacted composite layers comprises at least one of respective temperatures of the regions, respective first derivative rates of change of temperature of the regions over a plurality of digital thermographic images, and respective second derivative rates of change of temperature of the regions over a plurality of digital thermographic images, wherein the at least one heat characteristic of a subject region is different than surround regions if at least one of a peak of a second derivative rate of change of temperature for the subject region differs in time from a peak of a second derivative rate of change of temperature of at least one surrounding regions by more than a threshold amount or a peak in a first derivative rate of change of temperature for the subject region differs in time from a peak of a first derivative rate of change of temperature of at least one surrounding regions by more than a threshold amount; and
   upon identifying a defect region, outputting an alert.

2. The method of claim 1, further comprising:
   performing a repair on the defect region of the uncured compacted composite layers; and
   curing the compacted composite layers.

3. The method of claim 1, wherein analyzing at least one heat characteristic of the uncured compacted composite layers in the at least one digital thermographic image to identify regions in which the at least one heat characteristic is different than surrounding regions comprises analyzing at least one heat characteristic of every pixel in the at least one digital thermographic image.

4. The method of claim 1, wherein the alert includes an indication of a location of the defect region on the uncured compacted composite layers.

5. A system, comprising:
   a work surface for arranging and compacting uncured composite layers;
   a heat source arranged relative to the surface and operable to provide a burst of thermal energy to a surface of uncured compacted composite layers on the work surface;
   a thermographic digital camera arranged relative to the surface and operable to capture at least one digital thermographic image of the surface of uncured compacted composite layers on the work surface;
   a computer processor in communication with the thermographic digital camera and the heat source; and
   a computer memory containing a program that, when executed on the computer processor, performs an operation for processing data, comprising:
      outputting a signal to the heat source to apply a burst of thermal energy to a surface of uncured compacted composite layers;
      capturing at least one digital thermographic image of the surface of the uncured compacted composite layers after applying the burst of thermal energy;
      analyzing at least one heat characteristic of regions of the uncured compacted composite layers in the at least one digital thermographic image to identify defect regions in which the at least one heat characteristic is different than surrounding regions, wherein the at least one heat characteristic of the uncured compacted composite layers comprises at least one of respective temperatures of the regions, respective first derivative rates of change of temperature of the regions over a plurality of digital thermographic images, and respective second derivative rates of change of temperature of the regions over a plurality of digital thermographic images, and wherein the at least one heat characteristic of a subject region is different than surround regions if at least one of a peak of a second derivative rate of change of temperature for the subject region differs in time from a peak of a second derivative rate of change of temperature of at least one surrounding regions by more than a threshold amount or a peak in a first derivative rate of change of temperature for the subject region differs in time from a peak of a first derivative rate of change of temperature of at least one surrounding regions by more than a threshold amount; and
      upon identifying a defect region, outputting an alert.

6. The system of claim 5, wherein the program, when executed on the computer processor, performs an additional operation for processing data, comprising, upon receiving an indication of a repair being made to the defect region:

outputting a second signal to the heat source to apply a burst of thermal energy to a surface of uncured compacted composite layers;

capturing a second at least one digital thermographic image of the surface of the uncured compacted composite layers after applying the burst of thermal energy;

analyzing at least one heat characteristic of regions of the uncured compacted composite layers in the second at least one digital thermographic image to identify defect regions in which the at least one heat characteristic is different than surrounding regions; and upon identifying a defect region, outputting an alert.

7. The system of claim 5, wherein analyzing at least one heat characteristic of the uncured compacted composite layers in the at least one digital thermographic image to identify regions in which the at least one heat characteristic is different than surrounding regions comprises analyzing at least one heat characteristic of every pixel in the at least one digital thermographic image.

8. The system of claim 5, wherein the alert includes an indication of a location of the defect region on the uncured compacted composite layers.

9. A method, comprising:
arranging and compacting a plurality of uncured composite layers;
applying a burst of thermal energy to a surface of the plurality of uncured compacted composite layers;
capturing at least one digital thermographic image of the surface of the uncured compacted composite layers after applying the burst of thermal energy;
using a computer processor, analyzing at least one heat characteristic of regions of the uncured compacted composite layers in the at least one digital thermographic image to identify defect regions in which the at least one heat characteristic is different than surrounding regions, wherein the at least one heat characteristic of a subject region is different than surround regions if at least one of a peak of a second derivative rate of change of temperature for the subject region differs in time from a peak of a second derivative rate of change of temperature of at least one surrounding regions by more than a threshold amount or a peak of a first derivative rate of change of temperature for the subject region differs in time from a peak of a first derivative rate of change of temperature of at least one surrounding regions by more than a threshold amount; and upon identifying a defect region:
outputting an alert; and
performing a repair operation on the defect region.

10. The method of claim 9, further comprising curing the plurality of composite layers after performing the repair operation on the defect region.

11. The method of claim 9, further comprising:
after performing the repair operation on the defect region, arranging and compacting at least one additional uncured composite layer on the plurality of uncured composite layers to form a built-up plurality of uncured compacted composite layers;
applying a burst of thermal energy to a surface of the built-up plurality of uncured compacted composite layers;
capturing at least one digital thermographic image of the surface of the built-up uncured compacted composite layers after applying the burst of thermal energy;
using a computer processor, analyzing at least one heat characteristic of regions of the built-up uncured compacted composite layers in the at least one digital thermographic image to identify defect regions in which the at least one heat characteristic is different than surrounding regions;
upon identifying a defect region:
outputting an alert; and
performing a repair operation on the defect region.

12. The method of claim 11, further comprising curing the built-up plurality of composite layers after performing the repair operation on the defect region.

* * * * *